United States Patent [19]
Cong

[11] Patent Number: 6,087,181
[45] Date of Patent: Jul. 11, 2000

[54] SAMPLING AND DETECTION OF TRACE GAS SPECIES BY OPTICAL SPECTROSCOPY

[75] Inventor: Pejun Cong, Cupertino, Calif.

[73] Assignee: Symyx Technologies, Santa Clara, Calif.

[21] Appl. No.: 09/039,991

[22] Filed: Mar. 16, 1998

[51] Int. Cl.[7] .......................... G01N 21/41; G01N 21/45; G01B 9/02

[52] U.S. Cl. .............................. 436/37; 436/43; 436/52; 436/116; 436/127; 436/133; 436/134; 436/139; 436/141; 436/142; 436/147; 436/148; 436/155; 436/159; 436/171; 436/181; 356/349; 356/432

[58] Field of Search .................................. 436/37, 43, 52, 436/106, 116, 127, 133, 134, 139, 141, 142, 147, 148, 155, 159, 171, 181, 183; 356/346, 349, 432

[56] References Cited

FOREIGN PATENT DOCUMENTS 9611878  4/1996  WIPO .

OTHER PUBLICATIONS

P.L, Trevor etal, *Chem. Phys.* 1982, 68, 341–349.
A.J, Campillo etal, *Appl. Phys, Lett.* 1982, 41, 327–329.
M.J.D. Low etal, *J. Mol. Catal.* 1983, 20, 311–320.
J.A. Sell *Appl. Opt.* 1984, 23, 1586–1597.
A.C. Tam et al, *Chem. Phys. Lett.* 1985, 120, 280–284.
S.I. Yun et al. *Appl. Phys. B.* 1986, B40, 95–98.
S.A. Johnson et al. *Proc. SPIE–Int. Soc. Opt. Eng.* 1988, 917, 19–22.
R.M. Banish et al. *J. Appl. Phys.* 1988, 64, 2907–2916.
M.C. Gagne et al. *Appl. Phys. B.* 1991, B52, 352–358.
H.–J. Jung et al. *J. Korean Chem. Soc.* 1994, 38, 469–472.
A. Dreizler et al. *Chem. Phys. Lett.* 1995, 233, 525–532.
H.S.M. de Vries et al. *Rev. Sci. Instrum.* 1995, 66, 4655–4664.
M.Z. Silvg et al. *J. Phys.:Condens. Matter* 1995, 1, 9385–9399.
A, Dreizler et al. *Ber. Bunsen–Ges.* 1996, 100, 1678–1683.
Wu & Tong, "Forward–Scattering Degenerate Four–Wave Mixing as a Simple Sub–Attomole–Sensitive Nonlinear Laser Analytical Spectrometric Method," 65 *Analytical Chem.*, 112 (1993).
Thorsteinson et al., "The Oxidative Dehydrogenation of Ethane Over Catalysts Containing Mixed Oxides of molybdenum and Vanadium," *Journal of Catalysts*, 52, 116–132 (1978).
H.S.M. de Vries et al., "IR Laser Photothermal Trace Gas Detection Applied To Environmental and Biological Problems," *Infrared Phys. Technol.*, vol. 36, No. 1, pp. 483–488 (1995).
Zimering et al., "Applications of a compact photothermal––deflection–based setup for trace–gas detection in real–time in situ environmental monitoring and chemical analysis," *Applied Optics*, vol. 36, No. 15, (May 20, 1997), pp. 3188–3194.
H.M.S. de Vries, "Local Trace Gas Measurements by Laser Photothermal Detection; Physics Meets Physiology," PhD Thesis (Dec. 13, 1994).

*Primary Examiner*—Arlen Soderquist

[57] ABSTRACT

The present invention discloses a method for improving the speed and sensitivity of optical spectroscopic techniques for remote detection of trace chemical species in a carrier gas. The disclosed method can be applied to any optical spectroscopic detection technique whose sensitivity decreases as the total pressure of the sample decreases. The method employs an inert and non-absorbing buffer gas to supplement the pressure exerted by the carrier gas. This ensures that the total pressure of the sample, and hence sensitivity of the detection technique, remains high. The method is especially useful when measuring concentration of chemical species produced at small rates, and therefore should prove useful for rapid serial screening of combinatorial libraries of compounds.

42 Claims, 3 Drawing Sheets

SAMPLING AND DETECTION OF TRACE GAS SPECIES BY OPTICAL SPECTROSCOPY

BACKGROUND OF THE INVENTION

1. Technical Field

The present invention relates generally to systems for trace gas detection, and more particularly, to high-throughput screening of combinatorial libraries using an optical spectroscopy system.

2. Discussion

Combinatorial chemistry refers generally to a group of methods for creating chemical libraries—vast collections of compounds of varying structure—that are tested or screened in order to identify a subset of promising compounds. Libraries may consist of molecules free in solution, bound to solid particles, or arrayed on a solid surface.

Combinatorial chemistry has changed the way many scientists develop new and useful compounds. For example, workers in the pharmaceutical industry have successfully used such techniques to dramatically increase the speed of drug discovery. Material scientists have employed combinatorial methods to develop novel high temperature superconductors, magnetoresistors, and phosphors. More recently, scientists have applied combinatorial methods to aid in the development of catalysts. See, for example, copending U.S. patent application Ser. No. 08/327,513 "The Combinatorial Synthesis of Novel Materials" (published as WO 96/11878) and copending U.S. patent application Ser No. 08/898,715 "Combinatorial Synthesis and Analysis of Organometallic Compounds and Catalysts" (published as WO 98/03521), which are both herein incorporated by reference.

As with any new technology, combinatorial chemistry is not without problems. Once a researcher creates combinatorial libraries, he or she faces the daunting task of screening tens, hundreds or even thousands of compounds for one or more properties of interest. Although automating existing assays does provide a partial solution, traditional analytical methods are often ill-suited to screening large combinatorial libraries.

This is especially true in catalyst development, where, for a given reaction, the best catalysts are typically those that produce the most product in the shortest amount of time. Unlike traditional catalyst development, combinatorial methods do not permit the synthesis and testing of large amounts of a particular catalyst. Instead, minute quantities of each catalyst are typically deposited on a solid substrate—in the wells of a microtiter plate, for example—and the entire substrate is placed in a reaction vessel where individual catalysts are exposed to reactants. Catalyst library members thus comprise no more than about a few to a few hundred $\mu g$ of material, resulting in extremely small production rates ($\approx 1$ $\mu g/s$) and correspondingly low reaction product concentrations (<1 ppm).

Although the small production rates and low product concentrations associated with catalyst screening rule out many traditional analytical techniques, one viable approach is direct mass spectrometric detection, which is described in commonly assigned copending U.S. patent application Ser. No. 08/946,730, "Mass Spectrometers and Methods for Rapid Screening of Libraries of Different Materials," filed Oct. 8, 1997 (Attorney Docket No. 016703-000910), which is herein incorporated by reference. Other analytical techniques, such as photothermal detection spectroscopy and four-wave mixing spectroscopy, also appear promising because of their rapid response time and their ability to detect chemical species at extremely low concentrations (1–10 ppb). However, as discussed below, these optical spectroscopic methods, as currently practiced, are often unsuitable for screening combinatorial libraries.

Photothermal detection spectroscopy, which includes photothermal deflection, photoacoustic spectroscopy, thermal lensing, and interferometry, have been successfully used for trace gas detection. In all four methods, light from a cylindrical pump laser is passed through a sample containing a carrier gas and a chemical species of interest (analyte). Though the carrier gas is not directly affected by the laser light, the individual analyte molecules absorb the light energy and are "excited." The excited analyte molecules collide with neighboring carrier gas molecules, resulting in local heating in the vicinity of the laser light. The magnitude of the local heating is proportional to the number of excited analyte molecules, and can be used to determine the analyte concentration.

The four photothermal detection methods differ in the way the local heating is measured. For example, photothermal deflection spectroscopy (PTD) relies on a change in refractive index due to local heating of the sample gas. A second (probe) laser beam is directed into the locally heated region, and is deflected from its original path because of the change in refractive index. The degree of deflection can be measured, and is directly proportional to the concentration of the analyte. A general discussion of photothermal detection methods, and of PTD in particular, can be found in R. L. Zimering et al., 36 (15) *Applied Optics* 3188 (1997), and H. S. M. DeVries et al., 36(1) *Infrared Physics and Technology* 483 (1995), which are herein incorporated by reference.

Four-wave mixing spectroscopy is similar to PTD, thermal lensing, and interferometry in that it relies on local changes in the index of refraction of a sample gas. In a typical four-wave mixing setup, two laser beams are directed to intersect each other. In the overlap region, a periodic light intensity pattern (bright and dark) is created due to constructive and destructive interference of the two laser beams. At the crests of the light intensity pattern, more analyte molecules are excited than at the valleys of the intensity pattern. As in the case of the other thermal detection methods, the excited molecules collide with neighboring carrier gas molecules and the radiative energy absorbed is converted to thermal energy. The crest regions of the medium experience a higher temperature rise than the valley regions. Thus, the periodic light intensity pattern results in a spatially periodic temperature pattern, which for a gas medium, gives rise to a spatially equivalent, periodic density pattern. Since refractive index in the gas phase decreases with decreasing density, a refractive index grating is formed where the two laser beams overlap. This type of grating is commonly referred to as a thermal grating. When a third laser beam is directed at this refractive index grating, a portion of it is diffracted. The magnitude of the diffracted beam, which is detected as the signal, is a measure of the concentration of the analyte. There are a total of four laser fields involved, including the signal field, hence the name "four-wave mixing." This method is described in Wu & Tong, 65 *Analytical Chem.* 112 (1993), which is herein incorporated by reference.

Four-wave mixing and the photothermal detection methods are in many instances unsuitable for screening large libraries of catalytic materials because their sensitivity is limited by the sample pressure. For example, in PTD the signal strength, S, is related to the analyte concentration, C, and the sample total pressure, P, through the relationship:

$$S = \alpha \cdot C \cdot P \qquad \text{I}$$

where α is a proportionality constant. Given that there is some acceptable minimum value of S in which the signal strength is greater than some multiple of the background noise, decreasing the sample total pressure will result in an increase in the lower detection limit (LDL) of the analyte.

The loss in sensitivity with P is especially troublesome when screening combinatorial catalyst libraries through remote detection of C. As discussed above, the concentration of the analyte and its production rate at the catalyst surface are extremely low in combinatorial library screening. Therefore, researchers often use a capillary tube to transport the analyte from the catalyst surface within the reactor to a remote detection cell where they make the PTD measurement. The time it takes to fill the cell with the sample gas increases with decreasing pressure difference between the reactor and the detection cell. Assuming a 1 m long capillary tube with a 0.1 mm ID, a 1 cm³ detection cell, and a reactor pressure of 760 torr, the time to achieve a particular sample pressure within the detection cell and its affect on the lower detection limit of the analyte can be seen in Table 1.

TABLE 1

Dependence of Fill Time & Lower Detection Limit, LDL, on Sample Total Pressure, P

| P, torr | Time to Fill Cell with Sample, s | LDL, ppb |
|---|---|---|
| 1 | <1 | $5.8 \times 10^5$ |
| 10 | ≈10 | $5.8 \times 10^3$ |
| 100 | ≈100 | 58 |
| 760 | ∞ | 1 |

Thus, relatively long fill times are needed to detect chemical species below about 50 ppb, which would compromise the speed at which the catalyst library members are screened.

In situ detection might solve the problem of sensitivity loss with decreasing P, but its use with combinatorial library screening is problematic. Although catalytic products can be detected by directing the pump and probe laser beams within the reactor, the arrangement would result in an unacceptable loss of accuracy. Because of the low production rate of analyte, even if the detection volume (i.e., the region of local heating) is located about 1 mm above the catalyst surface, the measured concentration will be about a thousand-fold less than the concentration at the catalyst surface. Although library screening does not necessarily require knowledge of the analyte concentration at the surface of the catalyst, surface concentrations of 100 ppb or less would be undetectable since the lower detection limit of PTD is about 1 ppb. Moreover, in situ PTD measurements of combinatorial libraries are susceptible to cross contamination because adjacent catalysts are often no more than 2 mm apart. In such cases, cross contamination is likely if large disparities in catalytic activity exist between adjacent compounds.

The present invention is directed to overcoming, or at least minimizing, one or more of the problems set forth above.

SUMMARY OF THE INVENTION

In accordance with one aspect of the present invention, there is provided a method of improving the speed and sensitivity of remote detection of trace gas species using optical spectroscopy. The method includes the step of obtaining a gas sample that contains the trace gas species. The gas sample is introduced into a detection cell at a pressure lower than the sample source pressure. In a separate step, a buffer gas is added to the detection cell. Finally, the concentration of the trace gas species is measured using an optical spectroscopy technique, which provides a signal that is proportional to the amount of the trace gas species and the total pressure in the detection cell.

In accordance with a second aspect of the present invention, there is provided a method of remote detection of a trace gas species using optical spectroscopy. The trace gas species is obtained from a remote source and is contained in a carrier gas. The method includes the step of evacuating a detection cell to a total pressure less than the remote source pressure. A buffer gas is introduced in the detection cell so that the total pressure in the detection cell is less than the remote source pressure. In a separate step, the carrier gas containing the trace gas species is uniformly introduced in the detection cell while a series of measurements are made using an optical spectroscopy technique. The rate of change of the spectroscopy measurements with respect to time is proportional to the amount of the trace gas species in the detection cell.

In accordance with a third aspect of the present invention, there is provided a method for rapid serial screening of a combinatorial library of compounds. The method includes obtaining a gas sample, where the gas sample is associated with an element of the combinatorial library, which is typically from a region near the surface of a compound belonging to the combinatorial library. The gas sample is introduced into a detection cell at a pressure lower than the pressure near the surface of the member compound. In a separate step, a buffer gas is added to the detection cell. Finally, the amount of an analyte present in the gas sample is measured using an optical spectroscopy technique, which provides a signal that is proportional to the amount of the analyte and the total pressure in the detection cell. The amount of the analyte is an indicator of the performance of the member compound.

In accordance with a fourth aspect of the present invention, there is provided a method for rapid serial screening of a combinatorial library of compounds by detecting the presence of an analyte. The analyte is contained in a carrier gas, and the analyte—carrier gas sample is associated with a member of the combinatorial library, which is typically a region near the compound in the library. The method includes the step of evacuating a detection cell to a pressure less than the carrier gas source pressure. A buffer gas is introduced in the detection cell so that the total pressure in the detection cell is less than the carrier gas source pressure. In a separate step, the analyte and carrier gas are uniformly introduced in the detection cell while a series of measurements are made using an optical spectroscopy technique. The rate of change of the spectroscopy measurements with respect to time is proportional to the amount of the analyte in the detection cell. The amount of the analyte is an indicator of the performance of the member compound.

BRIEF DESCRIPTION OF THE DRAWINGS

The foregoing and other advantages of the invention will become apparent upon reading the following detailed description and upon reference to the drawings in which.

DETAILED DESCRIPTION OF THE PREFERRED EMBODIMENTS

The present invention helps avoid the loss of sensitivity with decreasing sample total pressure, P, by de-coupling P from the partial pressure of the carrier gas and analyte. In existing optical detection methods, P is composed of the partial pressure of the analyte, and the partial pressure of the carrier gas. As a result, the sensitivity of the methods depend on the amount of sample gas collected. This makes existing optical detection methods problematic for screening combinatorial libraries where low analyte production rates would require, in many cases, excessively long fill times to achieve the requisite sensitivity.

The present invention de-couples P from the partial pressure of the sample gas (analyte and carrier gas) by introducing the sample gas and a buffer gas in a remote detection cell in two steps. In this way, a chemist can minimize the relatively slow step of sample gas addition, but can ensure that the total pressure in the remote detection cell is large enough to obtain a detectable signal by adding the buffer gas in a relatively quick step. Although the chemist will not know a priori how little sample gas to collect, simple experimentation should indicate whether it can be decreased or whether it should be increased. The buffer gas can be the same as the carrier gas or different—it need only be inert in the system of interest, and should not absorb pump or probe laser light. Suitable buffer gases include, but are not limited to $N_2$, Ar, He, Ne, compressed air, and $CH_4$.

Improvement in sensitivity can be seen by comparing lower detection limits obtained with and without the use of a buffer gas. Assuming a 1 m long capillary sampling tube with a 0.1 mm ID, a 1 $cm^3$ detection cell, and a sample gas source pressure of 760 torr, the influence of the buffer gas on the lower detection limit of an analyte is illustrated in Table 2.

TABLE 2

Dependence of Lower Detection Limit, LDL, on Buffer Gas Partial Pressure, $P_B$, Sample Gas Partial Pressure, $P_S$, and Total Pressure in the Detection Cell, P

| $P_B$, torr | $P_S$, torr | P, torr | Time to Fill Cell With Sample, s | LDL, ppb |
|---|---|---|---|---|
| 0 | 1 | 1 | <1 | $5.8 \times 10^5$ |
| 759 | 1 | 760 | <1 | $7.6 \times 10^2$ |
| 0 | 10 | 10 | ≈10 | $5.8 \times 10^3$ |
| 750 | 10 | 760 | ≈10 | 76 |
| 0 | 100 | 100 | ≈100 | 58 |
| 660 | 100 | 760 | ≈100 | 7.6 |
| 0 | 760 | 760 | ∞ | 1 |

The greatest improvement in sensitivity occurs at the lowest values of sample gas partial pressure—about an 800-fold improvement in LDL when $P_S$ equals 100 torr. But even when $P_S$ equals 100 torr, the value of LDL with buffer gas is about one-eighth the value of LDL without the buffer gas. The data in Table 2 depend on the dimensions of the capillary tube, the volume of the detection cell, the magnitude of the source pressure, etc., and therefore should be considered illustrative and non-limiting.

Figure 1:
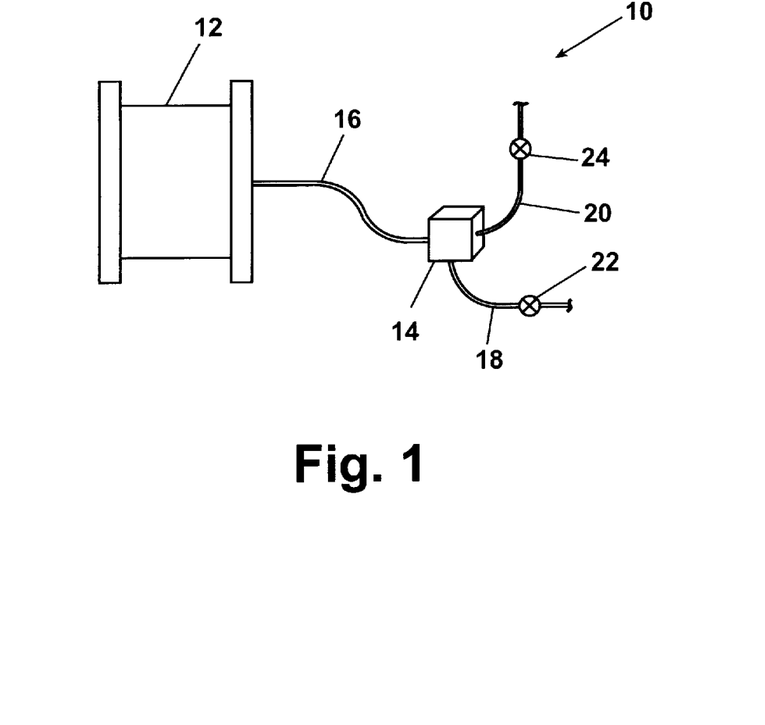
FIG. 1 schematically illustrates the basic components of an apparatus that can be used to screen a combinatorial catalyst library using photothermal deflection spectroscopy (PTD).
Figure 3:
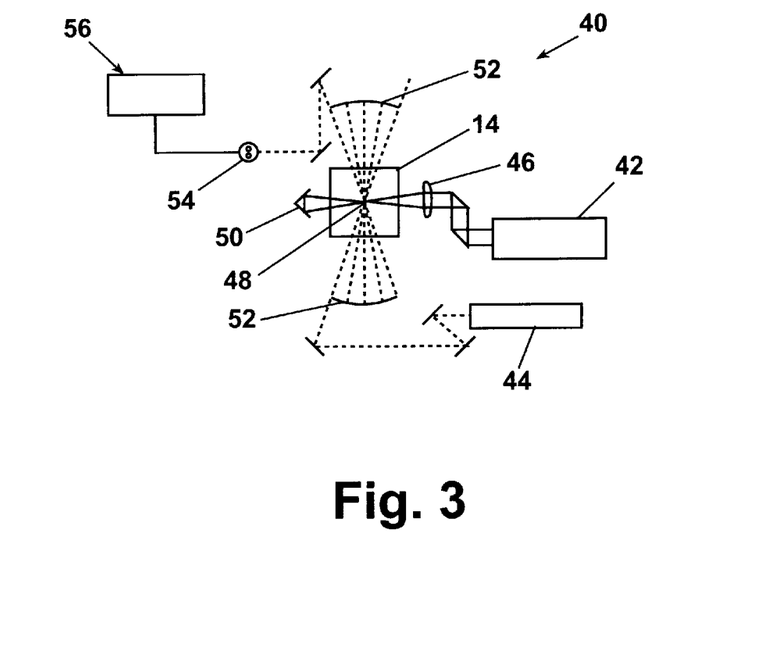
FIG. 3 schematically illustrates the components of a PTD system that can be used for remote detection of an analyte.

Referring now to the figures, FIG. 1 shows a schematic diagram of an apparatus 10 for screening a combinatorial library of catalysts using remote photothermal deflection spectroscopy. The apparatus 10 comprises a reaction chamber 12 and a remote detection cell 14. The volume of the remote detection cell 14 is large enough to accommodate an optical detection system, which is shown in FIG. 3 and described below. A conduit 16 transports sample gas from the reaction chamber 12 to the remote detection cell 14. The conductance of the conduit 16 is matched to the production rate of analyte at the surface of each catalyst.

The remote detection cell 14 is connected to a vacuum source through a vacuum line 18, and is connected to a buffer gas source (e.g., nitrogen) through a buffer gas line 20. A vacuum shut-off valve 22 is located in the vacuum line 18 between the remote detection cell 14 and the vacuum source, and is used to control the level of vacuum within the detection cell 14. Similarly, a buffer gas shut-off valve 24 is located in the buffer gas line 20 between the remote detection cell 14 and the buffer gas source, and is used to control the sample total pressure, P, in the detection cell 14. The vacuum shut-off valve 22 and the buffer gas shut-off valve 24 are both zero dead volume shut-off valves that allow the removal of analyte and the introduction of buffer gas without introducing extra volume.

Figure 2:
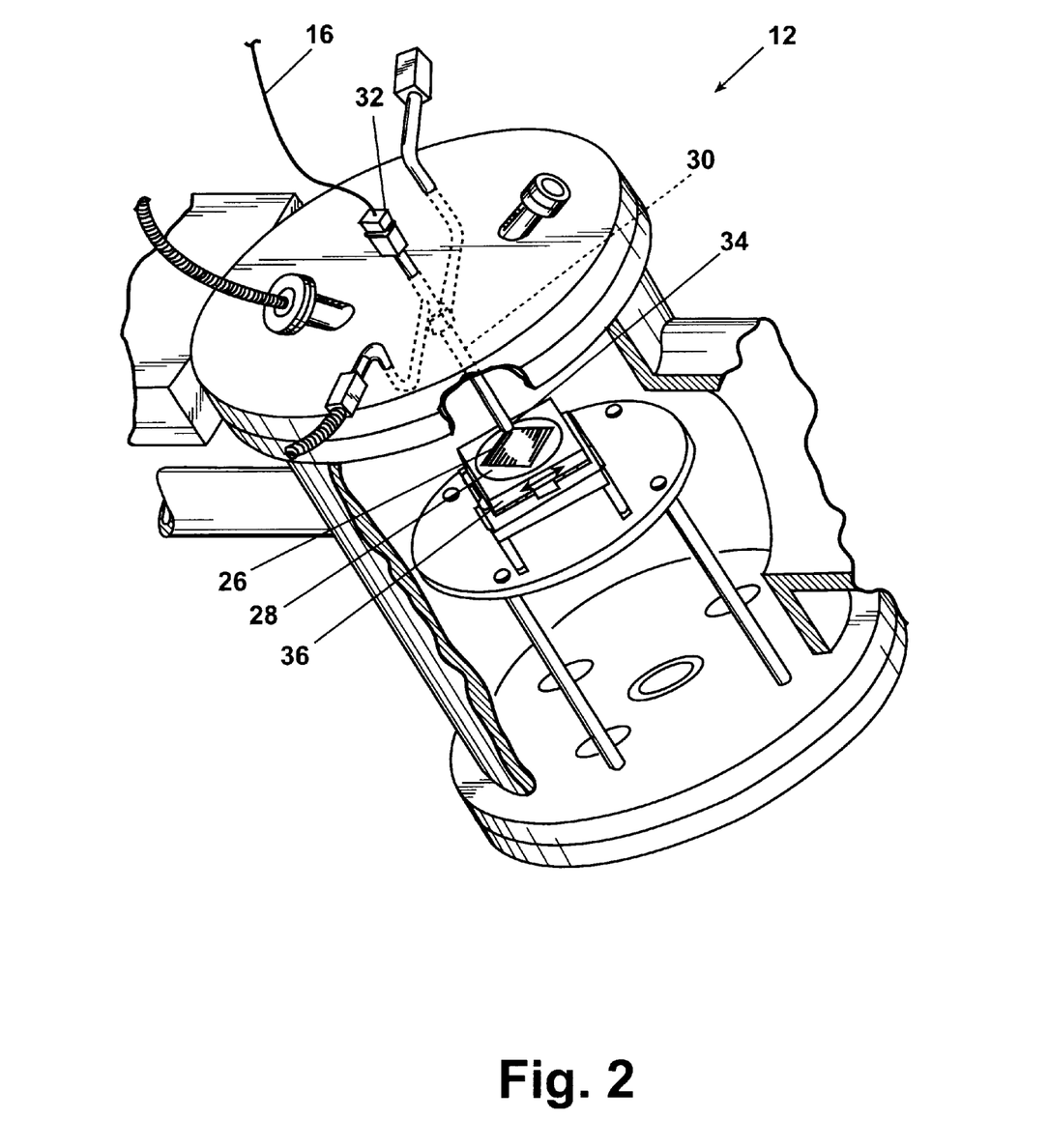
FIG. 2 shows a partial sectional view of a reaction chamber that can be used to screen a combinatorial catalyst library.

FIG. 2 shows a partial sectional view of the reaction chamber 12, which contains an array of catalysts 26 disposed at predefined positions on a solid substrate 28. A hollow probe 30 is used to withdraw gas samples containing the analyte. The probe 30 has a first end 32 attached to the conduit 16, and a second end 34 that is positioned above individual catalysts to sample reaction products. In the embodiment shown in FIG. 2, the probe is fixed within the reaction chamber 12 and can be positioned over a particular catalyst library member or region on the solid substrate 28 using a translation stage 36. A probe shut-off valve (not shown) can be used to stop the flow of sample gas through the probe 30.

FIG. 3 schematically illustrates the components of one illustrative photothermal deflection system 40 that can be used for remote detection of an analyte. The PTD system 40 consists of a line-tunable, $CO_2$ (pump) laser 42, and a He-Ne (probe) laser 44. Light from the $CO_2$ laser 42 is focused by a lens 46, and passes through the remote detection cell 14 containing the sample gas. A small portion of the energy from the $CO_2$ laser 42 is absorbed by the analyte molecules, resulting in a locally heated region 48; the remaining energy is absorbed by a $CO_2$ laser block 50. Light from the He-Ne laser 44 is directed into the locally heated region 48, and is deflected from its original path because of a change in refractive index of the sample gas. To improve the deflection signal, a pair of cylindrical mirrors 52 reflect light from the He-Ne laser 44 back through the locally heated region 48 numerous times. The degree of deflection is measured using a bicell detector 54. A signal from the bicell detector 54 is detected using a lockin amplifier 56. Note that the PTD system set-up is similar to that described in H. S. M. DeVries et al., 36(1) *Infrared Physics and Technology* 483 (1995).

Analyte concentration can be measured two ways. In a first embodiment, the analyte concentration is determined from signal strength. The remote detection cell 14 is evacuated by opening the vacuum shut-off valve 22, which is then closed. Sample gas flows from the reaction chamber 12 to the remote detection cell 14 through conduit 16 for a predetermined time. The amount of time can be adjusted to a desired value, but is generally in the range of 10 seconds to 100 seconds. The buffer gas shut-off valve 24 is opened.

Buffer gas flows into the remote detection cell 14 until the pressure in the detection cell 14 is the same as the pressure in the reaction chamber 12, and the buffer gas shut-off valve 24 is closed. A measurement of analyte concentration is then made using the PTD system. The concentration of the analyte, C, can be calculated from Equation I above, given the signal strength, S, the total pressure in the remote detection cell 14, P, and the value of α, which is determined by routine calibration.

In a second embodiment, the analyte concentrate is determined from the rate of increase in signal strength. The remote detection cell 14 is evacuated by opening the vacuum shut-off valve 22. Once the remote detection cell 14 is evacuated, the vacuum shut-off valve 22 is closed, the buffer gas shut-off valve 24 is opened, and buffer gas flows into the remote detection cell 14. The buffer gas shut-off valve 24 is kept open until the pressure within the detection cell 14 reaches a pre-selected value below the pressure of the reaction chamber 12, typically one-third to one-half the pressure of the reaction chamber 12. The probe shut-off valve is then opened, and while the sample gas flows into the remote detection cell 14, consecutive measurements of analyte concentration are made using the PTD system. Because the total pressure of the system remains nearly constant during the measurement step, the rate of the signal increase with time, $\dot{S}$, is proportional to the accumulation rate of the analyte in the detection cell. Or from Equation I, $$\dot{S} = k \cdot C \qquad \text{II}$$

where k is a constant and is determined by routine calibration. Generally, Equation II can be used to determine the amount of the analyte unless the analyte concentration is too low.

Either embodiment can be used to screen combinatorial libraries of catalysts. Typically, detection cell filling times range from about 10 seconds to about 100 seconds. Thus, for example, a library containing 144 samples can be screened in about 2 to 5 hours. Note, however, the disclosed technique is not limited to specific sampling rates or number of samples. Indeed, an important advantage of the disclosed measurement technique is its flexibility, allowing a chemist to adjust sampling rates by changing the detection cell filling time. In this way, the chemist can balance the need for improved sensitivity with the need to screen a large number of compounds.

Moreover, the measurement technique is not limited to screening combinatorial libraries of catalysts, but can be used for rapid serial screening of many different types of materials. For example, the disclosed method can be used to screen materials based on their ability to filter out a particular gas species. Such materials can be arrayed on a top surface of a porous substrate, while a bottom surface of the porous substrate is in contact with the gas species. If the bottom surface is held at a higher pressure than the top surface, and the substrate is masked so that gas can only flow through the array of materials, then the concentration of the gas species near the surface of a particular array element is a measure of that material's performance. Similarly, an array of polymeric materials synthesized using combinatorial methods can be screened for thermal stability by measuring the concentration of gas species produced at the surface of an array element when exposed to laser light. The amount of gas species (degradation products) evolved by a particular array element is a measure of that material's stability.

In addition to the use of nitrogen as the buffer gas, other gases can be used as long as they are inert and do not absorb light at the wavelengths of the pump and probe lasers. For example, Argon can be used as the buffer gas for a $CO_2$ pump laser and a He-Ne probe laser.

Generally, photothermal detection spectroscopy and four-wave mixing spectroscopy can be used to measure any gaseous compound that absorbs laser light. For example, $C_2H_4$, $NH_3$, $N_2H_4$, $CO_2$, $C_6H_6$, $C_7H_8$, HCOOH, $H_2S$, and many chlorofluorohydrocarbons absorb light in the 9 $\mu$m to 11 $\mu$m range, and therefore can be detected using a line-tunable $CO_2$ laser. Other molecules, such as CO and NO absorb light in the 5.3 $\mu$m to 5.9 $\mu$m range, and therefore can be detected using a line-tunable CO laser. The line-tunable laser can be exchanged for a continuously tunable laser including infrared radiation generated by optical parametric oscillation or optical parametric amplification. Generally, the laser can function at any suitable wavelength, including the visible and infrared regions.

EXAMPLES

The following examples are intended as illustrative and non-limiting, and represent specific embodiments of the present invention.

Example 1

Photothermal deflection spectroscopy detection using the disclosed sampling method is employed to measure ethylene production from dehydrogenation of ethane in the presence of a V-Mo-Nb catalyst deposited on a solid substrate. The optical detection system consists of a He-Ne probe laser, and a line-tunable $CO_2$ pump laser set to operate on the 10P14 $CO_2$ line (10.532 $\mu$m). The remote detection cell has about a 1 cm$^3$ volume. The catalyst is placed in a flow-reaction chamber whose pressure is maintained at 800 torr. Steady-state flow rates of $C_2H_6$, $O_2$ and $N_2$ through the reaction chamber are maintained at 1.6 sccm, 0.4 sccm and 2.0 sccm, respectively.

For each measurement, the remote detection cell is first evacuated for about 30 seconds using a turbo-molecular pump. The cell is then filled with effluent from the reaction chamber using a 3 m long capillary (65 $\mu$m ID) for another 30 seconds. Then, the cell is filled with $N_2$ to about 800 torr. Deflection of the He-Ne laser beam is measured by a bicell position-sensitive detector, and the deflection signal is processed by a lockin amplifier.

Measurements of ethylene concentration are made to determine the effect of heating on catalyst activity. Gas samples are taken from a region of the solid substrate containing no catalyst that is heated to various temperatures between 25° C. and 400° C. In all cases, the deflection signal is about 0.4 mV, indicating an ethylene concentration of about 10 ppm independent of temperature (the signal was calibrated through a separate series of experiments). A gas sample is then taken from a region near the surface of the catalyst heated to 400° C., and the deflection signal is 0.7 mV, indicating an ethylene level of about 17.5 ppm. When the temperature of the catalyst is decreased to 25° C., the measured signal is 0.5 mV. Thus, the net increase in catalytic activity due to heating is about 5 ppm.

Example 2

Photothermal deflection spectroscopy detection using the disclosed sampling method is employed to measure ethylene production from dehydrogenation of ethane in the presence of combinatorial library of V-Mo-Nb catalysts deposited on a solid substrate. Reaction conditions, sampling apparatus, and PTD detection system are the same as in Example 1, except that steady-state flow rates of $C_2H_6$, $O_2$ and $N_2$ through the reaction chamber were maintained at 0.8 sccm, 0.2 sccm and 1.0 sccm, respectively. Ethylene production is measured for each catalyst at 400° C., and is determined by measuring the rate of increase in signal strength.

For each measurement, the remote detection cell is first evacuated for about 30 seconds using a turbo-molecular pump. The cell is then filled with buffer gas to around 400 torr. Next, the cell is filled with effluent from the reaction chamber for about a minute, while the deflection signal is measured.

Figure 4:
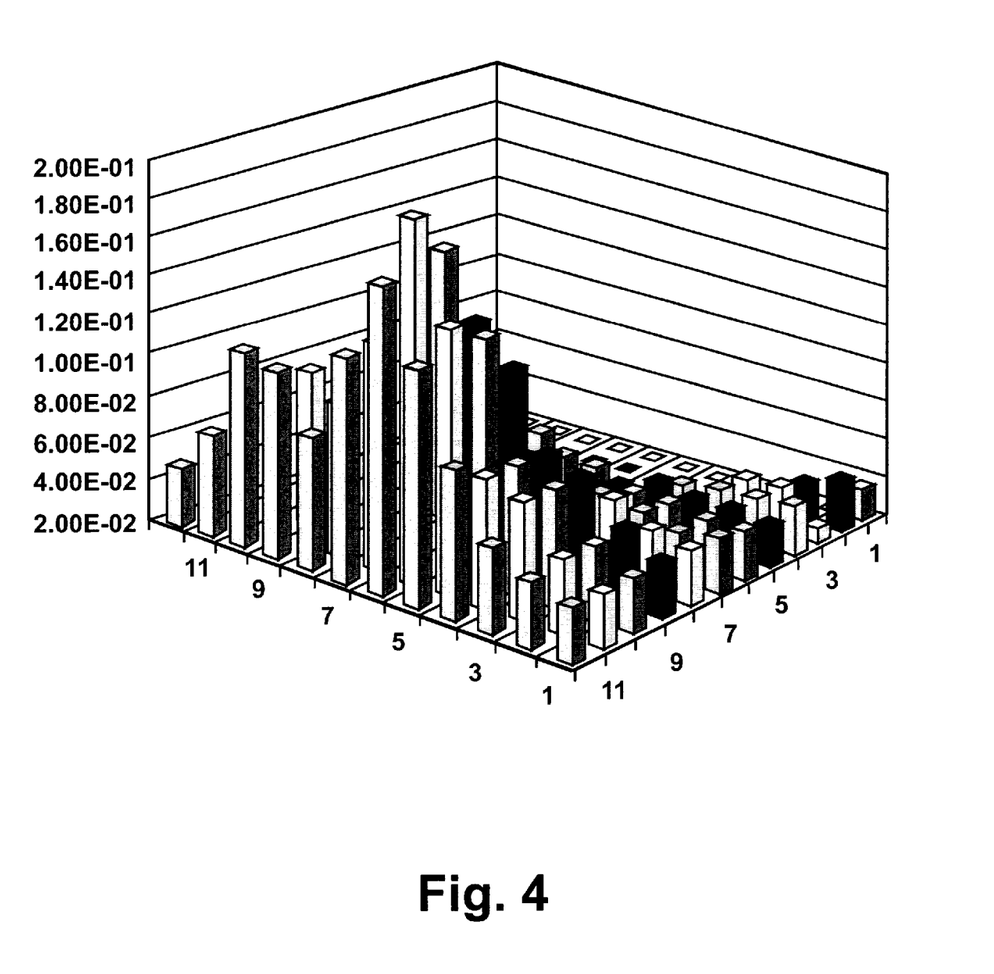
FIG. 4 illustrates measured ethylene production from a combinatorial catalyst library provided in Example 2.

FIG. 4 illustrates ethylene production (normalized) for V-Mo-Nb catalysts synthesized using combinatorial methods. The catalyst library consists of 66 different catalysts. Two copies of each catalyst are deposited on a solid support in two, 11×11×11 triangular arrays. For each triangular array, the front corner element contains 100% Mo, the left corner contains 50% Mo and 50% V, and the right corner contains 50% Mo and 50% Nb (all in their oxide forms). The composition of the maximum ethylene-producing catalyst is Mo70V25Nb5, which agrees with the optimum range reported in the literature.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method of improving the speed and sensitivity of remote detection of an analyte using an optical spectroscopy technique, the method comprising:

obtaining a sample gas containing the analyte from a remote source, the remote source having a pressure $P_o$;

introducing the sample gas containing the analyte in a detection cell at a pressure lower than $P_o$;

separately introducing a buffer gas in the detection cell at a rate faster than the sample gas containing the analyte so that the detection cell has a total pressure P;

detecting the analyte using the optical spectroscopy technique, wherein the optical spectroscopy technique is four-wave mixing spectroscopy or a photothermal detection method and produces a signal that depends on P.

2. The method of claim 1, wherein the signal is related to the amount of the analyte and the detection cell total pressure through the relationship $$S = \alpha \cdot C \cdot P$$

wherein S represents the signal, C represents the amount of the analyte, and α represents a constant that is determined by calibration.

3. The method of claim 1, wherein P is about equal to $P_o$.

4. The method of claim 1, wherein the optical spectroscopy technique is a photothermal detection method.

5. The method of claim 4, wherein the photothermal detection method is photothermal deflection spectroscopy.

6. The method of claim 1, wherein the optical spectroscopy technique is four-wave mixing spectroscopy.

7. The method of claim 1, wherein the remote source is a reaction chamber containing a catalyst and a reactant, and the analyte is a reaction product.

8. The method of claim 7, wherein the catalyst is a member of a combinatorial library of catalysts.

9. A method of improving the speed and sensitivity of detecting an analyte using an optical spectroscopy technique, the analyte contained in a carrier gas and obtained from a remote source at a pressure $P_o$, the method comprising:

evacuating a detection cell to a pressure less than $P_o$;

introducing a buffer gas in the detection cell, the buffer gas having a partial pressure $P_B$ in the detection cell such that $P_B$ is less than $P_o$;

inputting the carrier gas containing the analyte in the detection cell, wherein the carrier gas is introduced in the detection cell uniformly over a period of time at a rate slower than the buffer gas;

obtaining signals using the optical spectroscopy technique while inputting the carrier gas containing the analyte, wherein a rate of change of the signals with respect to time is proportional to the amount of the analyte, and the optical spectroscopy technique is four-wave mixing or a photothermal detection method.

10. The method of claim 9, wherein the amount of the analyte is related to the rate of change of the signals with respect to time through the relationship $$\dot{S} = k \cdot C$$

wherein $\dot{S}$ represents the rate of change of the signals with respect to time, C represents the amount of the analyte, and k represents a constant that is determined by calibration.

11. The method of claim 9, wherein the optical spectroscopy technique is a photothermal detection method.

12. The method of claim 11, wherein the photothermal detection method is photothermal deflection spectroscopy.

13. The method of claim 9, wherein the optical spectroscopy technique is four-wave mixing spectroscopy.

14. The method of claim 9, wherein the remote source is a reaction chamber containing a catalyst and a reactant, and the analyte is a reaction product.

15. The method of claim 14, wherein the catalyst is a member of a combinatorial library of catalysts.

16. The method of claim 9, wherein $P_B$ is less than about one-half of $P_o$.

17. The method of claim 16, wherein $P_B$ is more than about one-third of $P_o$.

18. A method of screening a combinatorial library, the combinatorial library having a total number of member compounds equal to N, the method comprising:

obtaining a gas sample associated with a member compound at a pressure $P_o$;

introducing the gas sample in a detection cell at a pressure lower than $P_o$;

separately introducing a buffer gas in the detection cell at a rate faster than the sample gas so that the detection cell has a total pressure P;

detecting an analyte contained in the gas sample using an optical spectroscopy technique, wherein the optical spectroscopy technique is four-wave mixing spectroscopy or a photothermal detection method and produces a signal that depends on P; and wherein the amount of the analyte is an indicator of the performance of the member compound.

19. The method of claim 18, wherein the signal is related to the amount of the analyte and the detection cell total pressure through the relationship $$S = \alpha \cdot C \cdot P$$

wherein S represents the signal, C represents the amount of the analyte, and α represents a constant that is determined by calibration.

20. The method of claim 18, wherein P is about equal to $P_o$.

21. The method of claim 18, wherein the optical spectroscopy technique is a photothermal detection method.

22. The method of claim 21, wherein the photothermal detection method is photothermal deflection spectroscopy.

23. The method of claim 18, wherein the optical spectroscopy technique is four-wave mixing spectroscopy.

24. The method of claim 18, wherein N is greater than ten.

25. The method of claim 18, wherein N is greater than one hundred.

26. The method of claim 18, wherein N is greater than one thousand.

27. The method of claim 18, wherein an average time to screen each member compound is less than one hundred fifty seconds.

28. The method of claim 18, wherein an average time to screen each member compound is less than one hundred seconds.

29. The method of claim 18, wherein an average time to screen each member compound is less than fifty seconds.

30. The method of claim 18, wherein the member compounds are catalysts, and the analyte is a reaction product.

31. A method of screening a combinational library by remote detection of an analyte using an optical spectroscopy technique, wherein the analyte is contained in a carrier gas, the combinatorial library has a total number of member compounds equal to N, and the analyte and the carrier gas are obtained at a pressure $P_o$, the method comprising:

evacuating a detection cell to a pressure less than $P_o$;

introducing a buffer gas in the detection cell, the buffer gas having a partial pressure $P_B$ in the detection cell such that $P_B$ is less than $P_o$;

inputting the carrier gas containing the analyte in the detection cell, wherein the carrier gas is introduced in the detection cell uniformly over a period of time at a rate slower than the buffer gas;

obtaining signals using the optical spectroscopy technique while inputting the carrier gas containing the analyte, wherein a rate of change of the signals with respect to time is proportional to the amount of the analyte, and the optical spectroscopy technique is four-wave mixing or a photothermal detection method; and wherein the amount of the analyte is an indicator of the performance of the member compound.

32. The method of claim 31, wherein the amount of the analyte is related to the rate of change of the signals with respect to time through the relationship $$\dot{S} = k \cdot C$$

wherein $\dot{S}$ represents the rate of change of the signals with respect to time, C represents the amount of the analyte, and k represents a constant that is determined by calibration.

33. The method of claim 31, wherein the optical spectroscopy technique is a photothermal detection method.

34. The method of claim 33, wherein the photothermal detection method is photothermal deflection spectroscopy.

35. The method of claim 31, wherein the optical spectroscopy technique is four-wave mixing spectroscopy.

36. The method of claim 31, wherein N is greater than ten.

37. The method of claim 31, wherein N is greater than one hundred.

38. The method of claim 31, wherein N is greater than one thousand.

39. The method of claim 31, wherein an average time to screen each member compound is less than one hundred fifty seconds.

40. The method of claim 31, wherein an average time to screen each member compound is less than one hundred seconds.

41. The method of claim 31, wherein an average time to screen each member compound is less than fifty seconds.

42. The method of claim 31, wherein the member compounds are catalysts, and the analyte is a reaction product.

* * * * *

UNITED STATES PATENT AND TRADEMARK OFFICE
CERTIFICATE OF CORRECTION

PATENT NO : 6,087,181
DATED : July 11, 2000
INVENTOR(S) : Peijun Cong

It is certified that error appears in the above-identified patent and that said Letters Patent are hereby corrected as shown below:

Title Page, [75] Inventor: "Pejun" --Peijun-- Cong

Signed and Sealed this

Twenty-fourth Day of April, 2001

*Attest:*

NICHOLAS P. GODICI

*Attesting Officer*     Acting Director of the United States Patent and Trademark Office